United States Patent
Bergh

(10) Patent No.: US 6,858,002 B2
(45) Date of Patent: Feb. 22, 2005

(54) SEXUAL AID

(76) Inventor: Ulf Bergh, Trastvägen 3, Södertälje (SE), S-152 70

(*) Notice: Subject to any disclaimer, the term of this patent is extended or adjusted under 35 U.S.C. 154(b) by 0 days.

(21) Appl. No.: 10/477,521
(22) PCT Filed: May 15, 2002
(86) PCT No.: PCT/SE02/00921
  § 371 (c)(1),
  (2), (4) Date: Nov. 20, 2003
(87) PCT Pub. No.: WO02/094141
  PCT Pub. Date: Nov. 28, 2002

(65) Prior Publication Data
  US 2004/0162464 A1 Aug. 19, 2004

(30) Foreign Application Priority Data
  May 22, 2001 (SE) .............................................. 0101815

(51) Int. Cl.[7] ................................................. A61F 5/00
(52) U.S. Cl. ....................................................... 600/38
(58) Field of Search ....................... 600/38–41; 604/346, 604/347, 349, 352–355; 128/885, 844, 918

(56) References Cited

U.S. PATENT DOCUMENTS

| | | | |
|---|---|---|---|
| 5,331,974 A | 7/1994 | Sook | 128/842 |
| 5,458,559 A | 10/1995 | Gauntlett | 600/38 |
| 5,836,865 A | 11/1998 | Ritchie et al. | 600/38 |
| 6,113,532 A | 9/2000 | Yap | 600/38 |

Primary Examiner—John P. Lacyk
(74) Attorney, Agent, or Firm—Jacobson Holman PLLC

(57) ABSTRACT

A sexual aid comprises a container arrangement (1) made of flexible sheet material and including two containers (10) each having a passageway (14) through which respective containers (10) can be filled with liquid. The containers are comprised of two flat-lain bags (10) which are disposed in at least partially overlapping relationship. The bags are joined together by two separate seams, to form an externally accessible space (15) between the bags. The neck (14) of respective bags has a length which enables respective necks (14) to be tied together in a knot (16).

8 Claims, 2 Drawing Sheets

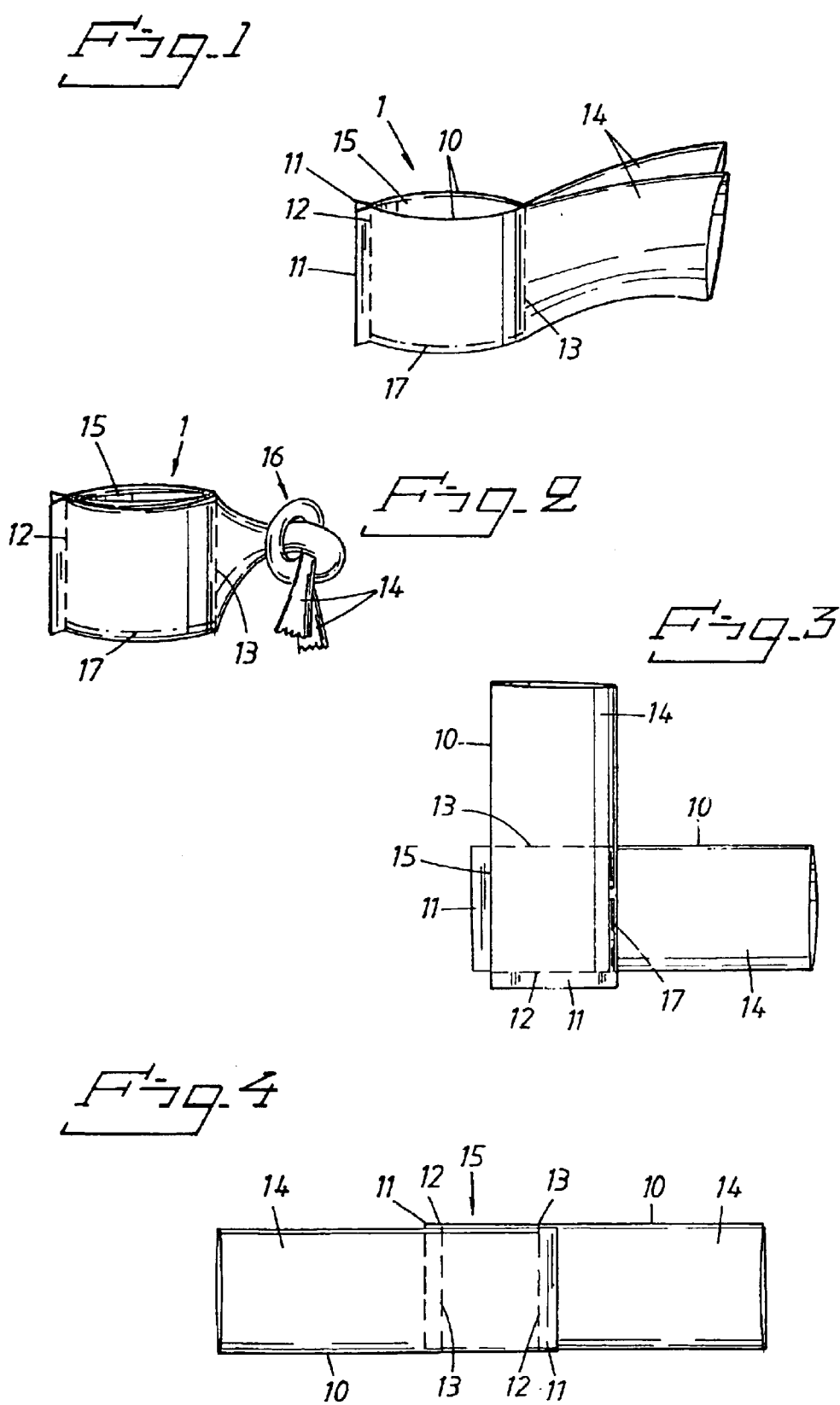

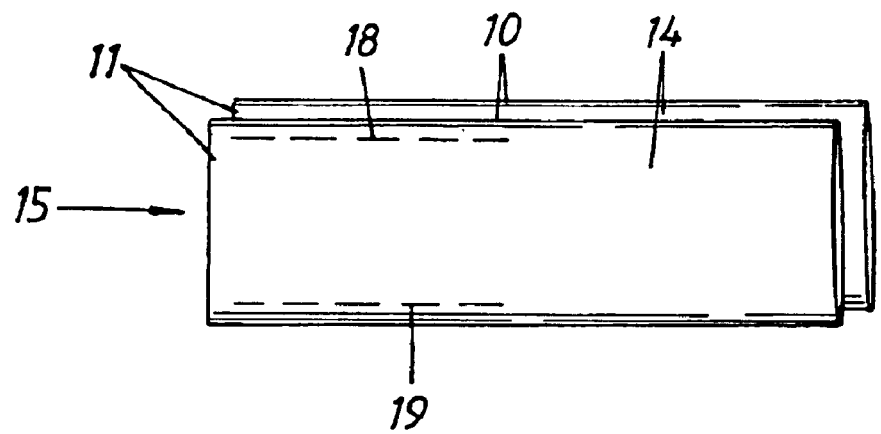
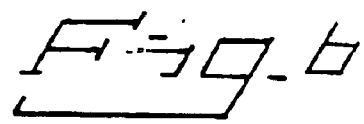
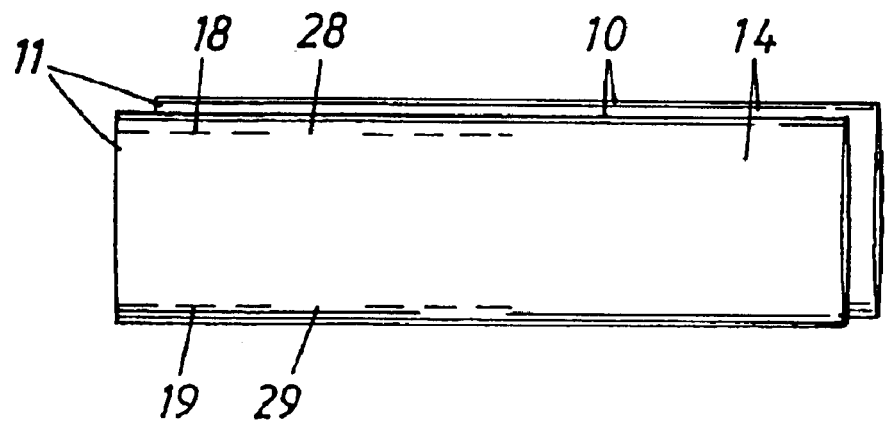

SEXUAL AID

This is a nationalization of PCT/SE02/00921 filed May 15, 2002 and published in English.

The present invention relates to a sexual aid of the kind defined in the preamble of the accompanying claim 1.

A known sexual aid of this kind includes a container unit or arrangement comprised of flexible sheet material, wherein the unit includes two containers that each have a respective filling passageway through which liquid can be delivered to respective containers, and wherein each passageway includes means for closing the passageway after having filled its respective container. Respective filling passageways consist of a tubular element which is welded firmly to its respective container and includes a stopper.

Such stopper-equipped filling tubes are relatively costly and require a working operation (welding) for connection through respective container walls. Moreover, the filling tube has a small throughflow capacity (whereby a relatively long period of time is required to fill the containers and spillage is often considerable). Insertion of the stopper in the filling tube also constitutes a troublesome task, when the tube has a small diameter.

The object of the present invention is to provide an aid of the aforementioned kind whose construction affords simple manufacture of the aid and also enables the containers to be filled with water quickly and the filling passageway easily closed.

The aid consists of a masturbation aid and is intended to liken a woman's vagina when filled with water of body temperature.

The object of the invention is achieved with the aid defined in claim 1.

Embodiments of the aid are defined in the accompanying dependent claims.

In one embodiment of the invention at present preferred, the aid is comprised of two flat, elongate bags which extend in mutually the same direction and which fully overlap one another, said bags being joined together by two welding seams, for instance along their respective long edges.

The neck portion of respective bags is sufficiently long to enable the necks to be readily sealed manually with a knot, for instance a half hitch, wherewith both necks can be sealed or closed-off simultaneously with a common knot, for example a common half hitch.

Since the bags may be produced with uniform width along their full length, the necks of the bags form filling passageways of large cross-sectional area, therewith enabling the containers to be readily and quickly filled with tepid tap water from the mains. The aid may be a disposable product, i.e. for one-time use only, and can be punctured in order to empty it of its liquid contents prior to being thrown away.

The invention will now be described by way of example with reference to the accompanying drawing.

FIG. 1 is a schematic perspective view of a first embodiment of an inventive aid.

FIG. 2 shows the aid according to FIG. 1 in an operative and liquid-filled state.

FIG. 3 is a schematic plan view of a second embodiment of an inventive aid.

FIGS. 4, 5, 6 are respective plan views of further embodiments of the inventive aid.

FIG. 1 illustrates two mutually similar, elongated flat bags 10 which are fully overlapping in their respective planes. Each plastic bag 10 has a bottom seam 11, which extends transversely to the longitudinal direction of the bag. The two bags 10 are joined together by a seam 12 which extends generally parallel with the bottom edge of respective bags 10 in the proximity of their bottom seams 11. An intermittent seam 13 connecting the bags 10 extends parallel with the seam 12. The seams 12, 13 and the two bags 10 define therebetween a space 15. The bags 10 have relatively long necks 14 outwardly of the seam 13. Tepid water can be delivered to the bag space between the space 12, 13, via the necks 14 and the gaps in the seam 13.

A further seam 17 may be provided to mutually join the bags 10 with their one edge region between the seams 12, 13. After having filled the bags 10 with liquid, the neck 14 of the bags may be commonly closed-off with a simple half hitch 16, as shown in FIG. 2.

As a variant of the embodiment shown in FIG. 1, the bags 10 may, instead, be comprised of lengths of flat-lain hoses, wherewith it is necessary for the seam 12 to form an end closure for each of the hoses, in addition to joining the hoses together.

FIG. 3 illustrates an embodiment corresponding to that shown in FIG. 1, with the exception that the flat-lain bags 10, such as lain in a common plane, define an angle of 90° between their respective long axes.

FIG. 4 illustrates an embodiment which corresponds to that shown in FIG. 1, with the exception that the bags 10 are positioned with their respective necks 14 extending in opposite directions.

FIG. 5 shows that the flat-lain bags 10 are preferably oblong in shape and preferably of mutually the same size and overlap each other essentially completely and have necks that face in mutually the same direction. The bag joining seams 18, 19 extend in respective length regions thereof, wherewith the space 15 obtains an access opening between the bottom ends 11 of the bags.

FIG. 6 illustrates an embodiment corresponding to FIG. 5. However, the seams 18, 19 of the FIG. 6 embodiment include interruptions 28, 29 which form access openings to the space 15 and which may have mutually different lengths.

A common feature of the illustrated embodiments is that the necks of the bags provide liquid filling passageways that have a large, free cross-sectional area, and that the necks can be readily closed-off, either individually or by knotting them together, for instance with a single half hitch, without requiring the use of any additional means to close the bags.

What is claimed is:

1. A sexual aid comprising a container arrangement or unit (1) made of flexible sheet material and including two containers (10), and individual passageways through which respective containers (10) are filled with liquid, wherein the containers (10) define therebetween a space (15) that has an accessible opening, characterised in that the containers consist of two bags which in a flat-lain state are intended to at least partially overlap one another; in that the bags are joined together by separate seams (12, 13; 18, 19); and in that each bag has a neck (14) which forms said filling passageway and which has a free length that enables the neck to be knotted with a knot (16), such as to close-off the bags.

2. An aid according to claim 1, characterised in that the bags are disposed in overlapping relationship with the necks of the bags parallel with one another.

3. An aid according to claim 1, characterised in that the bags are overlapped by similarly directed bag necks (14) which can be closed-off or sealed simultaneously with one and the same common knot, preferably a half hitch.

4. An aid according to claim 2, characterised in that at least one joining seam (13) that extends between the side edges of respective bags (10) is intermittent so as to allow liquid to be delivered to the major part of respective bags via said necks prior to sealing said necks.

5. An aid according to claim 1, characterised in that the space (15) formed between the two parallel seams (12, 13) and the bags (10) has the form of a throughpassing passageway.

6. An aid according to claim 1, characterised in that the space formed between the bags and the two parallel seams (12, 13) is delimited by a third joining seam (17) that extends transversely to the two generally parallel seams (12, 13).

7. An aid according to claim 2, characterised in that the bags are mutually joined by joining seams (18, 19) along their side-edge portions, which are directed parallel with the longitudinal axis of respective necks.

8. An aid according to claim 7, characterised in that at least one of the seams (18, 19) is interrupted (28, 29) between its ends, so as to form an access opening to the space (15) between the bags (10).

\* \* \* \* \*